United States Patent [19]

Spiewak et al.

[11] Patent Number: 4,669,459

[45] Date of Patent: Jun. 2, 1987

[54] ANTI-SNORING DEVICE

[76] Inventors: Martin H. Spiewak, 81 Maebelle Dr., Clark, N.J. 07066; Herbert Paskow, 1040 Wyandotte Trail, Westfield, N.J. 07090

[21] Appl. No.: 802,883

[22] Filed: Nov. 29, 1985

[51] Int. Cl.⁴ .............................................. A61F 5/56
[52] U.S. Cl. ................................................... 128/136
[58] Field of Search .................... 128/136, 132 R, 137

[56]  References Cited

U.S. PATENT DOCUMENTS

| 779,360 | 1/1905 | Gruman. | |
|---|---|---|---|
| 2,098,349 | 11/1937 | Henahan | 128/132 |
| 2,178,128 | 10/1939 | Waite | 128/136 |
| 3,224,442 | 12/1965 | Stubbs | 128/136 |
| 3,312,216 | 4/1967 | Wallshein | 128/136 |
| 3,312,217 | 4/1967 | McKinstry | 128/136 |
| 4,304,227 | 12/1981 | Samelson | 128/136 |
| 4,471,771 | 9/1984 | Steven et al. | 128/136 |
| 4,516,936 | 5/1986 | Hulsink | 433/6 |
| 4,519,386 | 5/1985 | Sullivan | 128/136 |

Primary Examiner—Robert A. Hafer
Assistant Examiner—Kathleen D'Arrigo
Attorney, Agent, or Firm—Popper, Bobis & Jackson

[57] ABSTRACT

An anti-snoring device includes at least two clasps, each clamping around an upper molar tooth on opposite sides of the mouth; a bridge made of an acrylic-like material connecting the clasps; a button which applies pressure to the soft palate of the person; and an easily bendable wire interconnecting the button and the bridge such that the button applies pressure to the soft palate to prevent vibration thereof.

8 Claims, 7 Drawing Figures

FIG. 1
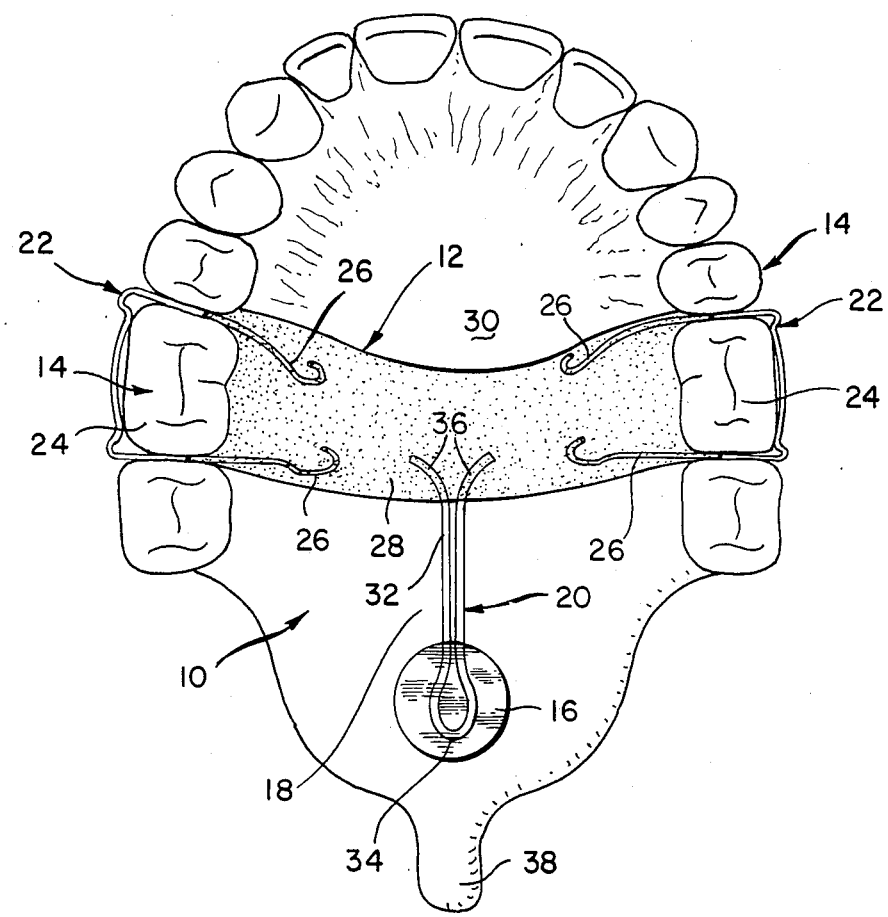
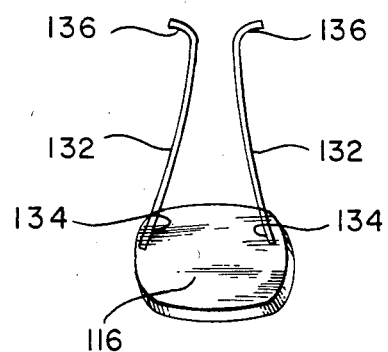
FIG. 2

FIG. 4
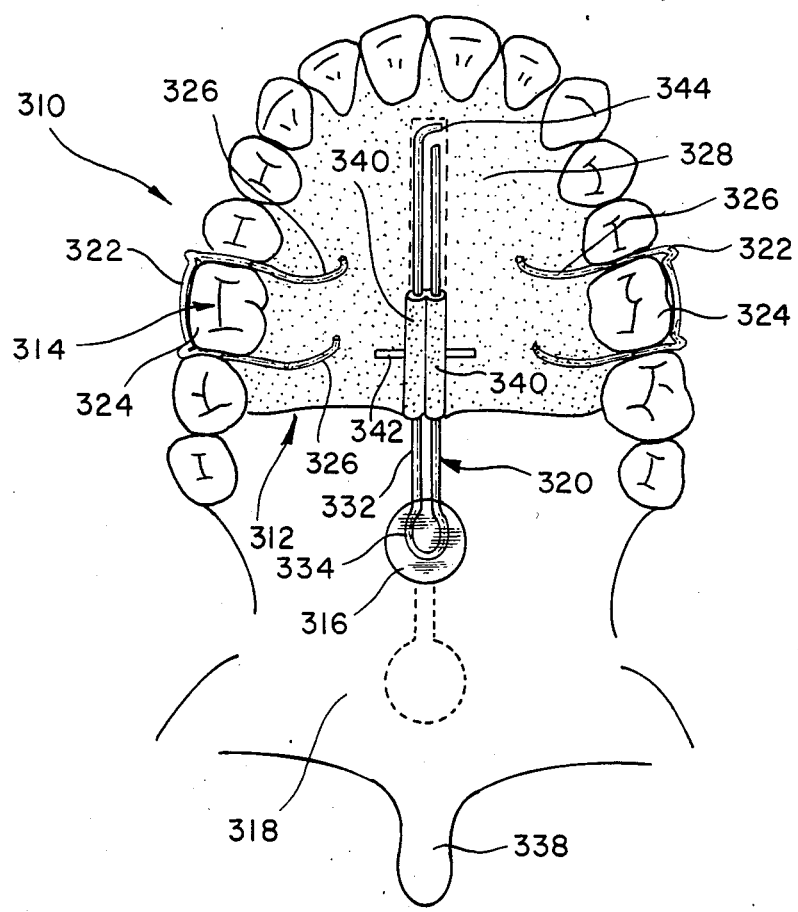
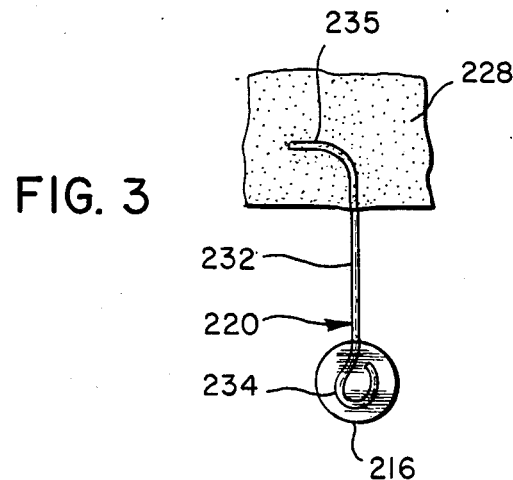
FIG. 3

FIG. 5
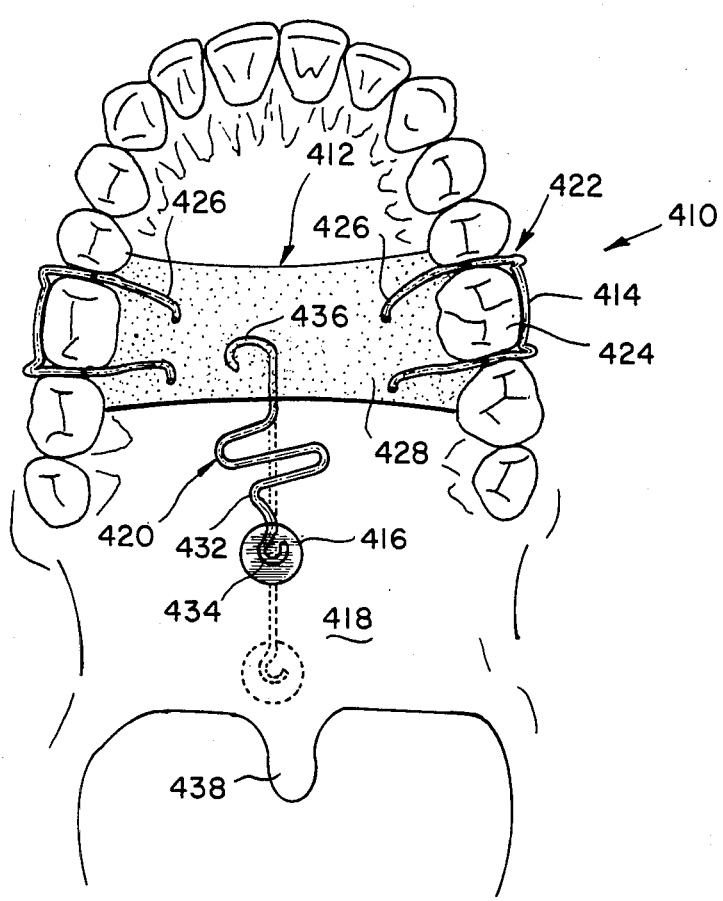
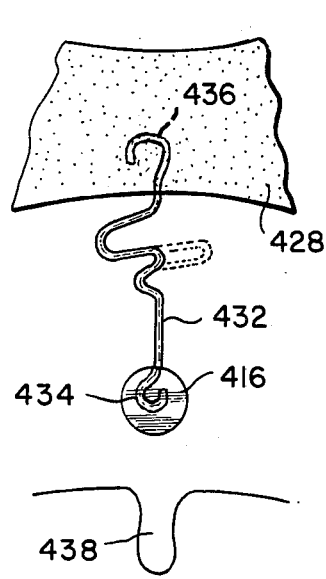
FIG. 6
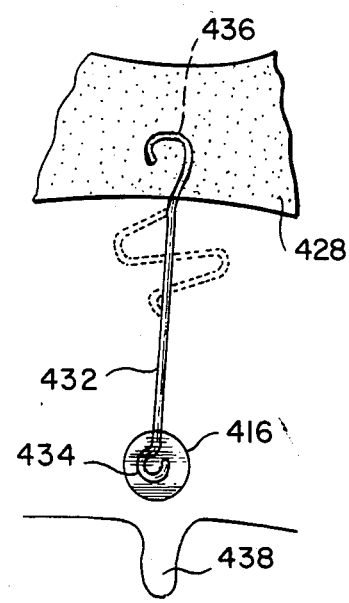
FIG. 7

ANTI-SNORING DEVICE

BACKGROUND OF THE INVENTION

The present invention relates generally to anti-snoring devices and, more particularly, is directed to an anti-snoring device which prevents vibration of the soft palate and uvula.

Generally, snoring occurs during sleep, causing annoyance to anyone within the sound range.

A problem with anti-snoring devices, however, is that there is the danger of swallowing the device when the person is asleep. Accordingly, anti-snoring devices have been relatively large and positioned only at the opening of the mouth for restricting the passage of air therethrough.

For example, U.S. Pat. No. 3,312,217 discloses an anti-snoring device which attaches to the person's chin so as to maintain the mouth in a closed position. U.S. Pat. No. 2,178,128 discloses a mouth piece having small air openings for restricting the passage of air to the mouth. In like manner, U.S. Pat. No. 4,304,227, discloses a mouth piece having air restriction means. See also U.S. Pat. No. 2,098,340.

For other devices which are not related to snore prevention, attention is directed to U.S. Pat. Nos. 779,360 (articulating instrument); 3,224,442 (weight repulsing appliance); 3,312,216 (tongue thrusting inhibiting device); 4,471,771 (oral weight control device); 4,516,936 (orthodontic device); and 4,519,386 (mouth splint).

OBJECTS AND SUMMARY OF THE INVENTION

Accordingly, it is an object of the present invention to provide a device for inhibiting snoring.

It is another object of the present invention to provide an anti-snoring device which provides minimal discomfort to the user.

It is still another object of the present invention to provide an anti-snoring device which does not substantially restrict the passage of air through the mouth or restrict normal swallowing while asleep.

It is yet another object of the present invention to provide an anti-snoring device which poses no danger to the user.

It is a further object of the present invention to provide an anti-snoring device which is easy and economical to manufacture and use.

In accordance with an aspect of the present invention, an anti-snoring device includes anchor means for securing the device in the mouth of a person; button means for applying pressure to the soft palate of the person; and extension means for connecting the button means to the anchor means such that the button means applies pressure to an effective portion of the soft palate to prevent vibration thereof.

In accordance with another aspect of the present invention, the extension means is adjustable to vary the length thereof, so that the button means can be adjusted for the individual person.

The above and other, objects, features and advantages of the present invention will become readily apparent from the following detailed description which is to be read in connection with the accompanying drawings.

BRIEF DESCRIPTION OF THE DRAWINGS

FIG. 1 is a bottom plan view of an anti-snoring device according to one embodiment of the present invention in assembled condition;

FIG. 2 is a perspective view of a modification of the anti-snoring device of FIG. 1;

FIG. 3 is a plan view of a further modification of the anti-snoring device of FIG. 1;

FIG. 4 is a bottom plan view of an anti-snoring device according to another embodiment of the present invention in assembled condition;

FIG. 5 is a bottom plan view of an anti-snoring device according to still another embodiment of the present invention in assembled condition;

FIG. 6 is a bottom plan view of a portion of the anti-snoring device of FIG. 5 in a partially extended position; and FIG. 7 is a bottom plan view of a portion of the anti-snoring device of FIG. 5 in a fully extended position.

DETAILED DESCRIPTION OF THE PREFERRED EMBODIMENTS

Referring to the drawings in detail, and initially to FIG. 1 thereof, an anti-snoring device 10 according to one embodiment of the present invention generally includes an anchor assembly 12 for securing the device to the upper posterior teeth 14 of a person, a button 16 for applying pressure to the soft palate 18 of the person, and an extension device 20 for connecting button 16 to anchor assembly 12 such that button 16 applies pressure to soft palate 18 to prevent vibration thereof. Specifically, button 16 applies only a slight pressure to the soft posterior section of soft palate 18 in order to prevent soft palate 18 from vibrating, thereby inhibiting snoring caused by the vibrating soft palate 18. The pressure that is applied, however, is not so great as to cause annoyance or discomfort to the person.

As shown, anchor assembly 12 includes molar clasps 22 which fit over upper molar, premolar or posterior teeth 24 on both sides of the mouth. Alternately, anchor assembly 12 may be connected to a person's partial or full upper denture or orthodontic appliance. As used hereinafter, references to the upper posterior teeth will also include such alternatives as connection to dentures or to the teeth through an orthodontic appliance. Although only two clasps are shown, more than two clasps 22 can be provided. Each molar clasp 22 includes free ends 26, which may be curved, and which extend partially past the inner surface of the respective molar tooth 24 into the mouth and toward the free ends 26 of the other molar clasp 22. A bridge 28 holds molar clasps 22. As an example, bridge 28 can be made of an acrylic or similar material, such as soft plastic, vinyl or the like, in which the free ends 26 of clasps 22 are embedded. Thus, bridge 28 covers a portion of the hard palate 30 of the person.

Button 16 is made of any suitable material such as acrylic or similar material and is shown having a circular form with a thickness of, for example, 2 to 5 mm, although button 16 is not so limited. Button 16 is connected to the center of bridge 28 by means of extension device 20 which may be formed by a bent wire 32 having the bend 34 thereof embedded within the acrylic material of button 16 and the free ends 36 thereof embedded within the acrylic material of bridge 28, centrally thereof, so as to position button 16, centrally at the posterior section of soft palate 18, in front of uvula 38. Extension device 20 is bent so as to provide a slight pressure on button 16 against the anterior or middle section of soft palate 18 to prevent vibration to the most effective area of the person's soft palate, and to thereby prevent snoring by the individual. It is to be noted that the soft palate moves while swallowing and the average individual swallows once each minute through the night. Therefore, the amount of such pressure may vary from zero to several ounces. Wire 32 should therefore be made of a soft metal which can be bent for, or even by, the individual user.

Accordingly, the present invention does not substantially inhibit the flow of air through the mouth and does not provide any great discomfort to the person. It must be realized that such an appliance may initially cause some gagging; but this reflex can be overcome with patience, diligence, practice and time.

Of course, various modifications can be made to the present invention within the scope of the claims herein. For example, as shown in FIG. 2, button 116 which is made of an acrylic or similar material, can have a different configuration to that shown in FIG. 1, as shown by the substantially rectangular configuration 116 in FIG. 2. In addition, two individual bent wires 132 can be provided having first ends 136 thereof embedded within a bridge 28 and opposite free ends 134 thereof embedded within the acrylic of button 116.

In addition, anchor assembly 12 may be formed, for example, similar to that shown in U.S. Pat. Nos. 4,519,386 and 3,312,216. Further, anchor assembly 12 may be formed to cover the entire hard palate portion (See FIG. 4) and/or be part of an orthodontic appliance, or it could be used in combination with a "bite-plate" or temporomandibular joint (TMJ) appliance commonly used by dentists and frequently prescribed by ear, nose and throat specialists.

Further, the entire combination of anchor assembly 12, bridge 28, extension device 20 and button 16 can be constructed as a single piece plastic assembly by any conventional process, such as die forming, injection molding and the like.

Still further, as shown in FIG. 3, extension device 220 can be formed from a single wire 232 which has one end bent, as at 234, embedded within button 216, and the other end bent, as at 235, and embedded in bridge 228.

Referring now to FIG. 4, an anti-snoring device 310 according to another embodiment of the present invention will now be described, in which elements similar to those in FIG. 1 are identified by the same reference numerals augmented by 300, and a detailed description of each of such similar elements will not be described herein for the sake of brevity. Specifically, extension device 320 in FIG. 4 differs from extension device 20 of FIG. 1 by being slidably connected to bridge 328, which also is modified to cover the entire hard palate.

As shown, extension device 320 includes two tubes 340 positioned parallel and adjacent to each other. Alternatively, tubes 340 can be connected to each other, for example, by soldering or the like, as shown in FIG. 4. A transverse bar 342 is secured midway across tubes 340 and is embedded in bridge 328. A bent wire 332 has the bend 334 embedded within button 316, as in the embodiment of FIG. 1, and the two extensions therefrom pass through tubes 340, respectively. One of the extensions of bent wire 332 can be bent at its free end, as shown at 344 to prevent bent wire 332 from escaping tubes 340. Thus, bent wire 332 can not be accidently swallowed by the user.

With this arrangement, bent wire 332 is slidable within tubes 340, as shown in dashed lines, whereby button 316 can be adjusted toward or away from uvula 338, on the soft palate, depending on the comfort, gag reflex and snoring control experience by the user. Thus, this device can be used to train the person to use the device, and can be gradually adjusted toward uvula 338. Of course, after bent wire 332 is adjusted, it will be bent to preferably apply slight pressure to the soft palate of the user and, because of such bending adjustment, will no longer slide within tubes 340. Additionally, wax can be placed at the opposite end of bent wire 332 extending from tubes 340, before extension device 320 is embedded in acrylic bridge 328 in order to fix the position thereof with respect to bridge 328, after extension device 320 is adjusted for the particular individual, while also permitting later adjustment of wire 332.

Refering now to FIGS. 5-7, an anti-snoring device 410 according to still another embodiment of the present invention will now be described in which elements similar to those in FIG. 1 are identified by the same reference numerals augmented by 400, and a detailed description of each of such elements will not be described herein for the sake of brevity. Specifically, extension device 420 in FIG. 5 includes a bent wire 432 having a first end with a bend 434 therein embedded within the acrylic material of button 416 and the opposite end 436 thereof embedded within bridge 428. Bent wire 432 is formed into different convolutions and, as aforesaid, is made of a soft, bendable material. In this manner, bent wire 432 can be unbent to the position shown in FIG. 6, in a partially extended position or can be fully unbent to the position shown in FIG. 7 where it is fully extended, depending upon the comfort to the user. This embodiment can be easily adjusted by the user.

Having described specific preferred embodiments of the invention with reference to the accompanying drawings, it is to be understood that the present invention is not limited to those precise embodiments, and that various changes and modifications may be effected therein by one of ordinary skill in the art without departing from the spirit and scope of the invention as defined by the appended claims.

What is claimed is:
1. An anti-snoring device comprising:
anchor means for securing said device in the mouth of a person;
button means for continuously applying pressure to the soft palate of the person; and
extension means fixedly connected to said button means and to said anchor means for controlling said button means to continuously apply pressure to an effective portion of the soft palate to prevent vibration thereof.
2. An anti-snoring device according to claim 1; wherein said anchor means includes clasp means on both sides of the mouth for clasping at least one upper posterior tooth of the person, and bridge means for interconnecting said clasp means.
3. An anti-snoring device according to claim 2; wherein said extension means includes wire means for connecting said button means to said bridge means at a central portion of the latter.
4. An anti-snoring device according to claim 3; wherein said bridge means is made of an acrylic material and said wire means is embedded therein.

5. An anti-snoring device according to claim 3; wherein said button means is made of an acrylic-like material and said wire means is easily bendable and is embedded therein.

6. An anti-snoring device according to claim 2; wherein said bridge means is made of an acrylic material and said clasp means on both sides of the mouth are embedded therein.

7. An anti-snoring device comprising:
 anchor means for securing said device in the mouth of a person;
 button means for continuously applying pressure to the soft palate of the person; and
 extension means connecting said button means to said anchor means for controlling said button means to continuously apply pressure to an effective portion of the soft palate to prevent vibration thereof, said extension means being slidably secured to said anchor means for slidably adjusting said button means in the mouth of the person.

8. An anti-snoring device according to claim 7; wherein said extension means includes tube means secured to said anchor means, and wire means slidably retained within said tube means; and wherein said button means is secured to said wire means and slidable therewith for adjusting said button means in the mouth of the person.

* * * * *